(12) United States Patent
Cheng et al.

(10) Patent No.: US 8,309,104 B2
(45) Date of Patent: Nov. 13, 2012

(54) ORAL CONTROLLED RELEASE FORMULATION FOR SEDATIVE AND HYPNOTIC AGENTS

(75) Inventors: Xiu Xiu Cheng, Weston, FL (US); Dacheng Tian, Miramar, FL (US)

(73) Assignee: Watson Pharmaceuticals, Inc., Corona, CA (US)

(*) Notice: Subject to any disclaimer, the term of this patent is extended or adjusted under 35 U.S.C. 154(b) by 706 days.

(21) Appl. No.: 11/712,133

(22) Filed: Feb. 28, 2007

(65) Prior Publication Data

US 2007/0207203 A1  Sep. 6, 2007

Related U.S. Application Data

(60) Provisional application No. 60/778,346, filed on Mar. 2, 2006.

(51) Int. Cl.
*A61K 9/00* (2006.01)
*A61K 9/52* (2006.01)
*A61K 9/22* (2006.01)

(52) U.S. Cl. .................. 424/400; 424/457; 424/468

(58) Field of Classification Search .......... 424/400, 424/457, 468
See application file for complete search history.

(56) References Cited

U.S. PATENT DOCUMENTS

| | | | |
|---|---|---|---|
| 3,577,514 A * | 5/1971 | Robinson | 424/468 |
| 4,327,725 A | 5/1982 | Cortese et al. | |
| 4,382,938 A | 5/1983 | Kaplan et al. | |
| 4,612,008 A | 9/1986 | Wong et al. | |
| 4,783,337 A | 11/1988 | Wong et al. | |
| 5,082,668 A | 1/1992 | Wong et al. | |
| 5,415,871 A | 5/1995 | Pankhania et al. | |
| 6,090,411 A * | 7/2000 | Pillay et al. | 424/468 |
| 6,514,531 B1 * | 2/2003 | Alaux et al. | 424/468 |
| 2002/0090394 A1 * | 7/2002 | Leonard et al. | 424/457 |
| 2003/0035839 A1 * | 2/2003 | Hirsh et al. | 424/471 |
| 2004/0258750 A1 | 12/2004 | Alaux et al. | |

OTHER PUBLICATIONS

Remington's Pharmaceutical Sciences, 17th edition, 1985, editor Alfonso R. Gennaro, p. 1306.*
Patricia A. Duff, "International Search Report", for PCT/US2007/005419, Sep. 8, 2008, 3 pgs., International Searching Authority, Alexandria, VA.
Patricia A. Duff, "Written Opinion of the International Searching Authority", for PCT/US2007/005419, Sep. 8, 2008, 3 pgs., International Searching Authority, Alexandria, VA.

* cited by examiner

*Primary Examiner* — Aradhana Sasan
(74) *Attorney, Agent, or Firm* — Florek & Endres PLLC

(57) ABSTRACT

The present invention relates to a novel controlled release dosage form that releases therapeutic amounts of a sedative or hypnotic agent rapidly after administration and maintains therapeutic levels for about eight hours after administration.

10 Claims, 6 Drawing Sheets

ORAL CONTROLLED RELEASE FORMULATION FOR SEDATIVE AND HYPNOTIC AGENTS

CROSS REFERENCE TO RELATED APPLICATION

This application claims the benefit of provisional application Ser. No. 60/778,346 filed on Mar. 2, 2006.

BACKGROUND OF THE INVENTION

1. Field of the Invention

The present invention relates to modified release dosage forms containing sedative and hypnotic agents, preferably short acting sedatives and hypnotic agents. The dosage form of the present invention should provide therapeutically effective amounts of the sedative or hypnotic agent relatively quickly and maintain therapeutic levels for about four to eight hours after administration.

2. Description of the Related Art

In today's fast pace, instant information society, there is an increase in stress and sleep disorders. A number of sedatives and hypnotics have been developed to manage and control stress and sleep disorders. Some of the more common sedatives and hypnotic agents commercially available are VALIUM, XANAX, AMBIEN, SONATA and LUNESTA. These commercially available pharmaceutical products provide immediate release of the active pharmaceutical ingredient after administration allowing an immediate effect on the patient, however, they often do not maintain the effect long enough for a patient to obtain the recommended eight hours of sleep.

Although controlled release pharmaceutical dosage forms which release therapeutic amounts of the active ingredient over 8 to 24 hours are well known in the pharmaceutical industry, there are very few that control the release of sedative or hypnotic agents in a manner that allows a patient to obtain therapeutic amounts of a sedative or hypnotic agent rapidly after administration and maintain the therapeutic levels for about eight hours after administration so that a patient can obtain a full eight hours of restful sleep.

One controlled release product that attempts to obtain therapeutic amounts of a sedative or hypnotic agent rapidly after administration and maintain the therapeutic levels for about eight hours after administration so a patient can obtain a full eight hours of restful sleep is AMBIEN CR. AMBIEN CR is a biphasic tablet wherein one layer provides an immediate release amount of zolpidem tartrate and the other layer provides a slow or controlled release of zolpidem tartrate. See AMBIEN CR labeling. It is believed that the AMBIEN CR product is described in U.S. Pat. No. 6,514,531. According to the teachings of U.S. Pat. No. 6,514,531, the bilayer tablet should release at least 40% of the zolpidem tartrate within 30 minutes when tested in a type II dissolution apparatus according to the U.S. Pharmacopoeia in 0.01M HCl buffer at 37° C. Bilayer tablets such as AMBIEN CR can be difficult to manufacture because they require the precise measurement of the drug into two distinct regions of a tablet press and the compressing of these distinct regions into a unitary tablet. According to the product labeling for AMBIEN CR, a further drawback of the AMBIEN CR product is that bioavailability, as measured by area under the curve (AUC) and maximum plasma concentration ($C_{max}$), was decreased by at least 20% and the median time to maximum plasma concentration ($T_{max}$) was increased from 2 to 4 hours when the AMBIEN CR bilayered tablet was administered within 30 minutes after a meal. This decrease in bioavailability resulted in a slower or delayed onset of sleep.

United States Published Patent Application No. 2004/0258750 discloses another attempt to prepare a suitable controlled release dosage form for sedative and hypnotic agents. United States Published Patent Application No. 2004/0258750 discloses a multi-particulate dosage form that comprises a combination of immediate release pellets and delayed release pellets. The delayed release pellets are prepared by coating a drug core with a coating that is impermeable to the drug on contact with aqueous fluids but that breaks down or becomes permeable to the drug after a suitable period of time. As with the bilayered AMBIEN CR tablet, the multi-particulate dosage forms described in United States Published Patent Application No. 2004/0258750 can be difficult to manufacture.

SUMMARY OF THE INVENTION

The present invention is a novel controlled release dosage form that releases therapeutic amounts of a sedative or hypnotic agent rapidly after administration and maintains therapeutic levels for about four to eight hours after administration. The present invention also relates to a method for manufacturing the aforementioned controlled release dosage form.

The dosage form prepared according to the present invention should release less than 40%, preferably not more than 35% and most preferably not more than 30% of the sedative or hypnotic agent within 30 minutes when tested according to the United States Pharmacopiea 29 using Apparatus II (paddles), 900 ml of 0.01 N HCl at 50 rpms and 37° C.

The dosage form of the present invention can be a tablet or capsule. The tablet can be mono or multi phasic, i.e two or more layers. The dosage form of the present invention can also be prepared from a plurality of beads, pellets or mini tablets that are formulated to release the sedative or hypnotic agent in the aforementioned manner. The beads, pellets or mini tablets can be a homogeneous population, i.e the beads, pellets or mini tablets have the same ingredients and composition or a heterogeneous population, i.e more than one type of bead, pellet or mini tablet. The beads, pellets or mini tablets can be placed into a gelatin capsule or mixed with conventional tableting excipients and compressed into a tablet.

It is also an object of one embodiment of the present invention to provide a controlled release dosage form that is monophasic with respect to the sedative or hypnotic agent. As used herein, monophasic means that the sedative or hypnotic agent is present in a homogeneous or unitary form. For example the present invention, prior to administration, does not employ multiple layers or multiple components where the sedative or hypnotic agent is present in different concentrations, or with different excipients. The fact that the present invention is monophasic results in a much simpler manufacturing process than the process described in the prior art.

It is a further object of the present invention to provide a controlled release dosage form that does not exhibit substantial differences in bioavailability when the dosage form is administered under fed (non-fasting) and fasting conditions. More specifically, it is an object of one embodiment of the present invention to provide a dosage form that does not exhibit a substantial decrease in AUC, $C_{max}$ and/or and increase in $T_{max}$ when the dosage form is administered within 30 minutes of a meal.

The foregoing objectives and others are obtained by an embodiment of the present invention that comprises a unitary core and optionally a functional coating surrounding the unitary core. In one embodiment of the present invention, the unitary core comprises a pharmaceutically acceptable sedative or hypnotic agent and a matrix forming material. The matrix forming material maybe a hydrogel polymer or a hydrophobic material combined with water soluble materials to aid in the hydration of the hydrogel or formation of pores in the hydrophobic material. If a functional coating surrounding the unitary core is employed it should, but not necessarily, comprises a pH dependent material and/or a pore forming material. The pH dependent material and the pore forming material can be the same component depending upon the composition of the coating selected. In one embodiment of the present invention the pH dependent material of the coating comprises about 10% or less of the total weight of the final dosage form, preferably about 7.5% or less of the total weight of the final dosage form and most preferably about 5% or less of the total weight of the final dosage form. The term functional coating as used in this application means a coating that affects the release of the drug from the core of the dosage form, i.e the tablet core or the bead or pellet core. The functional coating does not include coatings applied solely for aesthetic reasons such as a wax polishing coat.

Other objects, features and advantages of the invention are not taught in the prior art but will be more apparent to those versed in the art from the following specifications, taken in conjunction with the accompanying claims.

BRIEF DESCRIPTIONS OF DRAWINGS

FIG. 1 is a graph depicting the dissolution profile of the formulation as described in Example 1 and of a commercially available AMBIEN CR product (Lot #WJ22) when tested in a USP apparatus 2 using 900 ml of 0.01N HCl at 50 rpms and 37° C.

DETAILED DESCRIPTION OF THE INVENTION

Figure 1:
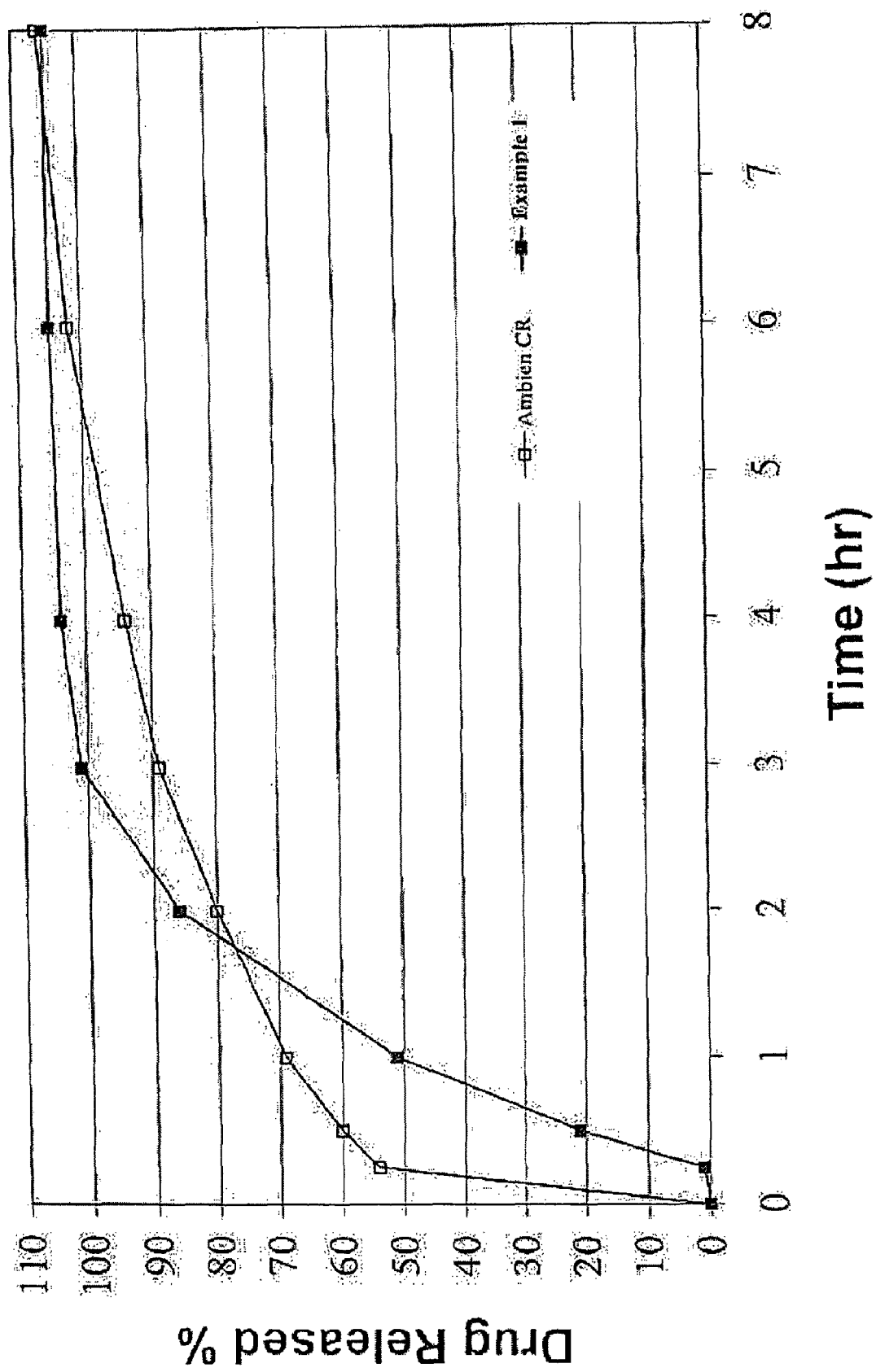

One embodiment of the present invention is a controlled release oral dosage formulation for sedatives and hypnotic agents that comprises a unitary core and optionally a coating that surrounds the core. The core may comprise an effective amount of a sedative or hypnotic agent and a controlled release matrix forming material. The optional coating preferably comprises a pH dependent material and/or a pore forming material.

Examples of some of the sedatives useful in the present invention include: barbiturates such as mephobarbital, pentobarbital and secobarbital and benzodiazepines such as flurazepam, estazolam, diazepam, alprazolam, triazolam, temazepam and brotizolam. Examples of some hypnotics useful in the present invention include: pyrazolopyrimidines such as zaleplon; cyclopyrrolones such as zopiclone and its enatiomers like (eszopiclone); phenothiazines such as alimemazine and imidazopyridines such as zolpidem. Other sedatives and hypnotic agents are described in Remington, The Science and Practice of Pharmacy $20^{th}$ ed., pages 1408-1420 and The Merck Index $13^{th}$ ed., pages Ther-28-29 which are incorporated herein by reference. A preferred embodiment of the present invention employs the hypnotic agents selected from pyrazolopyrimidines, cyclopyrrolones, phenothiazines, imidazopyridines or combinations of the foregoing. A more preferred embodiment of the present invention employs hypnotic agents selected from the group consisting of zaleplon, zopiclone, eszopiclone, alimemazine, zolpidem and combinations of the foregoing. The most preferred hypnotic agent is zolpidem.

It should be understood that the forgoing description of the sedatives and hypnotic agents also includes all pharmaceutically acceptable salts and isomers of the sedative and hypnotic agents.

The core may also comprise a matrix forming material. The matrix forming material can be a hydrophobic material such as a wax or insoluble plastic. Examples of some of the hydrophobic materials that can be used for the matrix material are carnauba wax, bees wax, gylceryl behenate, hydrogenated castor oil, and gylceryl stearates such as glyceryl monostearate. The matrix forming material can also be a hydrophilic material such as ethylcellulose, acrylic polymers and copolymers such as Eudragit RS, RL NE30, cellulose acetate, cellulose acetate butyrate, polyvinyl chloride, polyvinyl acetate, hydroxypropyl methylcellulose, hydroxyethylcellulose, hydroxypropyl cellulose, methylcellulose, polyvinylpyrrolidone(povidone), polyethylene oxide. In the case of beads, pellets or mini tablets the core can be prepared by laying the sedative or hypnotic agent onto an inert carrier such as a sugar sphere or microcrystalline cellulose, extruding and spherionizing the sedative or hypnotic agent with a binder or conventional blending and/or granulating of the sedative and hypnotic agent with conventional excipients.

In a preferred embodiment, the matrix forming material is a hydrogel or material that swells and/or gels in the presence of water or gastro-intestinal fluids. Examples of the hydrogel materials are provided in U.S. Pat. Nos. 5,082,668, 4,783,337, 4,612,0008 and 4,327,725 which are incorporated herein by reference. Some of the preferred hydrogel materials are polyvinyl pyrrolidone, methylcellulose, hydroxymethyl cellulose, polyethylene oxide polymers, hydroxyethyl cellulose, hydroxypropyl cellulose, hydroxypropyl methylcellulose (HPMC) and mixtures of the foregoing. The preferred matrix forming material is a water soluble polymer that swells in the presence of water or gastro-intestinal fluids and has a molecular weight between 5,000 and 1,000,000. It is also preferred that the matrix forming material exhibit a viscosity in a 2% aqueous solution of about 1,000 cps to about 120,000 cps, preferably about 2,000 cps to about 50,000 cps and most preferably about 3,000 cps to about 15,000 cps. The amount of matrix forming material will vary depending upon the drug, molecular weight and amount of other excipients present in the unitary core. In one embodiment of the present invention, the matrix forming material comprises about 1 to about 50% of the total weight of the unitary core, preferably about 2 to about 25% of the total weight of the unitary core and most preferably about 3 to about 15% of the total weight of the unitary core.

The core may optionally contain a diluent or filler. If a diluent is employed in the core, it can be any type of diluent commonly known in the art such as sugars, starches or vegetable oils. Examples of some preferred diluents are lactose, calcium carbonate, calcium sulfate, microcrystalline cellulose, calcium phosphate, dextrin, dextrose, maltitol, maltose, starch, sucrose or talc. If the core is prepared with a hydrophobic matrix material, a water soluble diluent should be used so that pores or channels can be created in the matrix to aid in the release of the sedative or hypnotic agent. In a preferred embodiment of the present invention, the diluent used in the core of the tablet is a combination of water soluble materials and water insoluble materials such as microcrystalline cellulose and lactose. If a diluent is used in the core, the total amount of diluent ranges from about 1% to about 95% of the total weight of the core, preferably 25% to 90% of the total weight of the core, and most preferably about 40% to about 85% of the total weight of the core. If a combination of water soluble and water insoluble diluents are used in the unitary core the ratio of water soluble to water insoluble diluent should range from 5:1 to 1:5, preferably, 3:1 to 1:3 and most preferably about 1:2 to about 2:1.

The unitary core may also optionally contain lubricants and glidants. Lubricants and glidants are used to facilitate manufacturing of the formulation, some examples of suitable lubricants and glidants include, talc, calcium stearate, magnesium stearate, stearic acid, glyceryl behenate, polyethylene glycol and colloidal silicon dioxide. The lubricants and glidants are preferably comprise about 0.05 to about 15% of the total weight of the core, preferably about 0.1 to about 10% of the total weight of the core and most preferably about 0.5 to about 5% of the total weight of the core.

Other conventional excipients may be used in the core such as stabilizers, antifoaming agents, colorants and dispersing aids.

The unitary core of one embodiment of the present invention is preferably formed by mixing the core ingredients until a homogeneous mixture is obtained and tableting the mixture using techniques commonly known in the art. The unitary core may also be formed by granulating some or all of the core ingredients and compressing the granules with or without the addition of a lubricant into a tablet. The tableting can be preformed on a rotary press.

Once the core is formed, a coating may be applied by conventional coating techniques, such as compression coating, pan coating or fluid bed coating. A preferred embodiment applies the coating to the core by first creating a solution, suspension or dispersion of a polymeric material in water or suitable organic solvents. The coating comprises a pH dependent material and/or a pore forming material. The pH dependent material and the pore forming material may be the same compound. The coating may also comprise a water insoluble polymer.

The term "pH dependent" as used in this application refers to materials that dissolve only within specified pH ranges and not over the entire pH spectrum. For example many commonly known enteric polymers do not dissolve in the acidic stomach environment. Other pH dependent polymers, such as Eudragit E, are designed to dissolve at low pH's, i.e below a pH of 5. The pH dependent material is selected so that when it is incorporated into the coating, it facilitates the release of the pharmaceutically active ingredient from the unitary core. The coating comprises about 1 to about 20 weight percent of the final dosage form, preferably about 2 to about 15 weight percent of the final dosage form and most preferably about 3 to about 10 weight percent of the final dosage form. Some of the pH dependent materials employed in the coating are preferably enteric polymers such as zein, methacrylic acid copolymers such as ACRYL-EZE and Eudragit S, cellulose acetate phthalate, hydroxypropyl methylcellulose phthalate, hydroxypropyl methylcellulose acetate succinate, cellulose acetate trimellitate, polyvinyl acetate phthalate or mixtures thereof. Other pH dependent polymers that are useful in the present invention include methacrylic polymers that are soluble in pH's below 5, such as dimethylaminoethyl methacrylate and methacrylic acid esters commercially available under the Tradename Eudragit E.

The amount of pH dependent material in the pH dependent coating is preferably about 30 to about 99 weight percent of the total weight of the coating, preferably about 40 to about 90 weight percent based on the total weight of the coating and most preferably about 50 to about 80 weight percent based upon the total weight of the coating.

The coating may also employ a water insoluble polymer material such as ethylcellulose, cellulose acetate, polyvinyl acetate or a polymethacrylate such as ammoniomethacrylate copolymers commercially available under the tradename Eudragit RL and Eudragit RS or a neutral polymethacrylic acid ester such as Eudragit NE 30D. If a water insoluble polymer and a pH dependent/pore forming material is used in the coating the ratio of water insoluble material to pH dependent/pore forming material should be about 3:1 to 1:3, preferably between 2:1 and 1:2, most preferably about 1:1.5 to about 1.5:1.

The pore forming material employed in the coating may be a water soluble or rapidly dispersible material that is capable of dissolving or leaching from the coating to enable water and/or gastro-intestinal fluid to permeate the coating and interact with the core. Some examples of the pore forming materials are sugars and sugar derivatives such as lactose, sucrose, fructose, mannitol, sorbitol, water soluble polymers such as hydroxypropyl methylcellulose, hydroxypropyl cellulose, polyvinyl pyrrolidone, polaxmers, surfactants such as sodium lauryl sulfate and tween, organic acids such as fumaric acid, succinic acid and citric acid and inorganic salts such as sodium chloride and potassium chloride. Other possible pore forming materials include the aforementioned pH dependent materials, especially the materials that dissolve at a pH below 5. The amount of the pore forming material employed in the coating is preferably about 1 to about 70 weight percent of the total weight of the coating, preferably about 10 to about 60 weight percent based on the total weight of the coating and most preferably about 20 to about 50 weight percent based upon the total weight of the coating.

The coating may also contain plasticizers. Plasticizers which may be used include any of those known to those skilled in the art, including but not limited to, acetyltributyl citrate, triacetin, acetylated monoglyceride, rape oil, olive oil, sesame oil, acetyltriethyl citrate, glycerin sorbitol, diethyloxalate, diethylmalate, diethylfumerate, dibutylsuccinate, diethylmalonate, dioctylphthalate, dibutylphthalate, dibutylsebacate, triethyl citrate, tributylcitrate, glyceroltributyrate, polyethylene glycol, propylene glycol and mixtures thereof. The preferred plasticizer is acetyltributyl citrate and triethyl citrate.

The coating may further include conventional processing aids and conventional excipients such as anti-foaming agents, dispersing aids, surfactants, anti-sticking agents, colorants, pigments and polishing aids.

The dosage form prepared according to the present invention should release less than 40% of the sedative or hypnotic agent within 30 minutes when tested according to the United States Pharmacopiea 29 using Apparatus II (paddles), 900 ml of 0.01 N HCl at 50 rpms and 37° C. In a preferred embodiment the dosage form of the present invention should exhibit the following dissolution profile when tested in a USP apparatus 2 using 900 ml of 0.01N HCl at 50 rpms and 37° C.

| DRUG RELEASED | | |
|---|---|---|
| Time (hours) | Preferred | Most Preferred |
| 0.25 | 0-15% | 0-10% |
| 0.5 | NMT† 35% | NMT 30% |
| 1 | 30-75% | 40-70% |
| 2 | NLT* 45% | NLT 50% |
| 4 | NLT 50% | NLT 60% |
| 8 | NLT 85% | NLT 90% |

†NMT = Not More Than
*NLT = Not Less Than

DESCRIPTION OF THE PREFERRED EMBODIMENTS

EXAMPLE 1

A 12.5 mg zolpidem tartrate tablet in accordance with the present invention was prepared as follows:

(a) Core 10.2 kg of microcrystalline cellulose (AVICEL PH 102), 2.380 kg of hydroxypropyl methylcellulose (METHOCEL K4M Premium CR Grade), 1.7 kg of zolpidem tartrate, 19.30 kg of anhydrous lactose (direct tableting grade) and 0.085 kg of colloidal silicon dioxide (CAB-O-SIL M-5P) were loaded into a three cubic foot V-Blender and blended for 20 minutes. The blended material was then passed through a comil fitted with an 1143 size stainless steel screen operating at a speed of about 1400 rpm. The screened material was blended in the three cubic foot blender for an additional 20 minutes. 0.34 kg of magnesium stearate was screened with a 30 mesh screen and added to the three cubic foot blender and blended for an additional 5 minutes. After all the ingredients were blended together, the mixture was compressed into tablets using a rotary press fitted with 0.3125" round standard concave punches. The target hardness was between 4-12 kp with a target weight of 250 mg.

The core tablets were coated with a pH dependent coating as follows:

(b) pH Dependent Coating 0.5525 kg of hydroxypropyl cellulose (KLUCEL EF) was added to approximately 19.89 kg of purified water and mixed until the hydroxypropyl cellulose was dissolved. Once the hydroxypropyl cellulose was dissolved approximately 1.657 kg of an enteric methacrylic acid copolymer (ACRYL-EZE White) was added to the solution while mixing at high speed. The mixing continued for about 20 minutes until the enteric polymer was uniformly dispersed. The enteric polymer dispersion was applied to the core tablets prepared in step (a) using a 36" pan coating apparatus. The pan coater employed three spray guns located about 5-12 inches from the tablet bed, a pan speed of 3-14 rpms, a spray rate of 40-150 ml/min, an atomization pressure of 25-45 PSI, a pattern pressure of 25-45 PSI, air volume of 300-1200 CFM and an exhaust temperature of 35-55 C. The coating continued until the weight gain on 100 tablets was about 0.875 g-1.625 g per tablet (i.e target of 1.250 g per 100 tablets). Once the target weight gain was obtained the tablets were rotated at 2-4 rpms for about 5 minutes to dry. Approximately 0.0136 kg of Candelilla wax was then applied to the tablets in the pan coater.

The final tablet had the following composition:

| Ingredient | mg/tablet |
|---|---|
| Core | |
| Zolpidem tartrate | 12.5 |
| Methocel K4M PCR | 17.5 |
| Avicel PH 102 | 75.0 |
| Anhydrous Lactose DC | 141.9 |
| Cab-O-Sil | 0.6250 |
| Mg Stearate | 2.5 |
| Coating | |
| Acryl-Eze White | 9.375 |
| Klucel EF | 3.125 |
| Candelilla Wax* | 0.10 |

*part of aesthetic coating (polishing)

Dissolutions studies for drug release from the formulation of Example 1 were conducted using a USP apparatus 2, 900 ml of 0.01N HCl at 50 rpms and 37° C. The results of the dissolution testing are:

| Time | % dissolved |
|---|---|
| 0.25 hour | 1 |
| 0.5 hours | 21 |
| 1 hours | 51 |
| 2 hours | 86 |
| 3 hours | 101 |
| 4 hours | 104 |
| 6 hours | 105 |
| 8 hours | 105 |

A graph depicting the dissolution profile is shown in FIG. 1. A graph showing the dissolution profile of the biphasic AMBIEN CR product under similar conditions is also shown in FIG. 1.

The tablet prepared in Example 1 was tested on 48 individuals in a single dose study according to FDA bioequivalence guidelines. The reference product for the study was a commercially available AMBIEN CR tablet. A summary of the biostudy results are reproduced below:

EXAMPLE 1

N=47 (Fasting)

| | Ln - Transformed Data | | | | | |
|---|---|---|---|---|---|---|
| | Least Squares Mean | | Geometric Mean | | | 90% Confidence Level |
| PK Variable | Test | Reference | Test | Reference | % Ratio | (Lower Limit, Upper Limit) |
| $C_{max}$ | 5.313 | 5.095 | 202.96 | 163.15 | 124.41 | (117.41, 131.82) |
| $AUC_{0-t}$ | 6.615 | 6.657 | 746.01 | 778.10 | 95.88 | (90.55, 101.52) |
| $AUC_{0-\infty}$ | 6.626 | 6.671 | 754.20 | 789.22 | 95.56 | (90.2, 101.25) |

| | Non-Transformed Data | | | |
|---|---|---|---|---|
| | Least Squares Mean | | | 90% Confidence Level |
| PK Variable | Test | Reference | % Ratio | (Lower Limit, Upper Limit) |
| $C_{max}$ | 214.38 | 172.18 | 124.51 | (117.54, 131.48) |
| $AUC_{0-t}$ | 818.30 | 856.51 | 95.54 | (89.57, 101.51) |

-continued

| PK Variable | Test | Reference | % Ratio | (Lower Limit, Upper Limit) |
|---|---|---|---|---|
| $AUC_{0-\infty}$ | 827.71 | 869.57 | 95.19 | (89.05, 101.32) |
| $T_{max}$ | 1.94 | 1.58 | 122.61 | (106.94, 138.27) |
| $k_e$ | 0.3014 | 0.2583 | 116.65 | (111.49, 121.81) |
| $t_{1/2}$ | 2.53 | 2.99 | 84.60 | (78.67, 90.54) |

EXAMPLE 1

N=48 (Non-Fasting)

Ln - Transformed Data

| PK Variable | Least Squares Mean Test | Least Squares Mean Reference | Geometric Mean Test | Geometric Mean Reference | % Ratio | 90% Confidence Level (Lower Limit, Upper Limit) |
|---|---|---|---|---|---|---|
| $C_{max}$ | 5.003 | 4.855 | 148.80 | 128.33 | 115.95 | (108.66, 123.74) |
| $AUC_{0-t}$ | 6.463 | 6.462 | 641.19 | 640.27 | 100.14 | (93.56, 107.19) |
| $AUC_{0-\infty}$ | 6.477 | 6.475 | 650.09 | 649.04 | 100.16 | (93.64, 107.14) |

Non-Transformed Data

| PK Variable | Least Squares Mean Test | Least Squares Mean Reference | % Ratio | 90% Confidence Level (Lower Limit, Upper Limit) |
|---|---|---|---|---|
| $C_{max}$ | 156.84 | 136.64 | 114.78 | (108.23, 121.34) |
| $AUC_{0-t}$ | 705.03 | 704.84 | 100.03 | (92.83, 107.23) |
| $AUC_{0-\infty}$ | 715.28 | 716.03 | 99.90 | (92.71, 107.08) |
| $T_{max}$ | 2.91 | 3.55 | 81.85 | (72.22, 91.48) |
| $k_e$ | 0.2845 | 0.2806 | 101.37 | (96.08, 106.66) |
| $t_{1/2}$ | 2.82 | 2.91 | 96.68 | (90.07, 103.29) |

Figure 2:
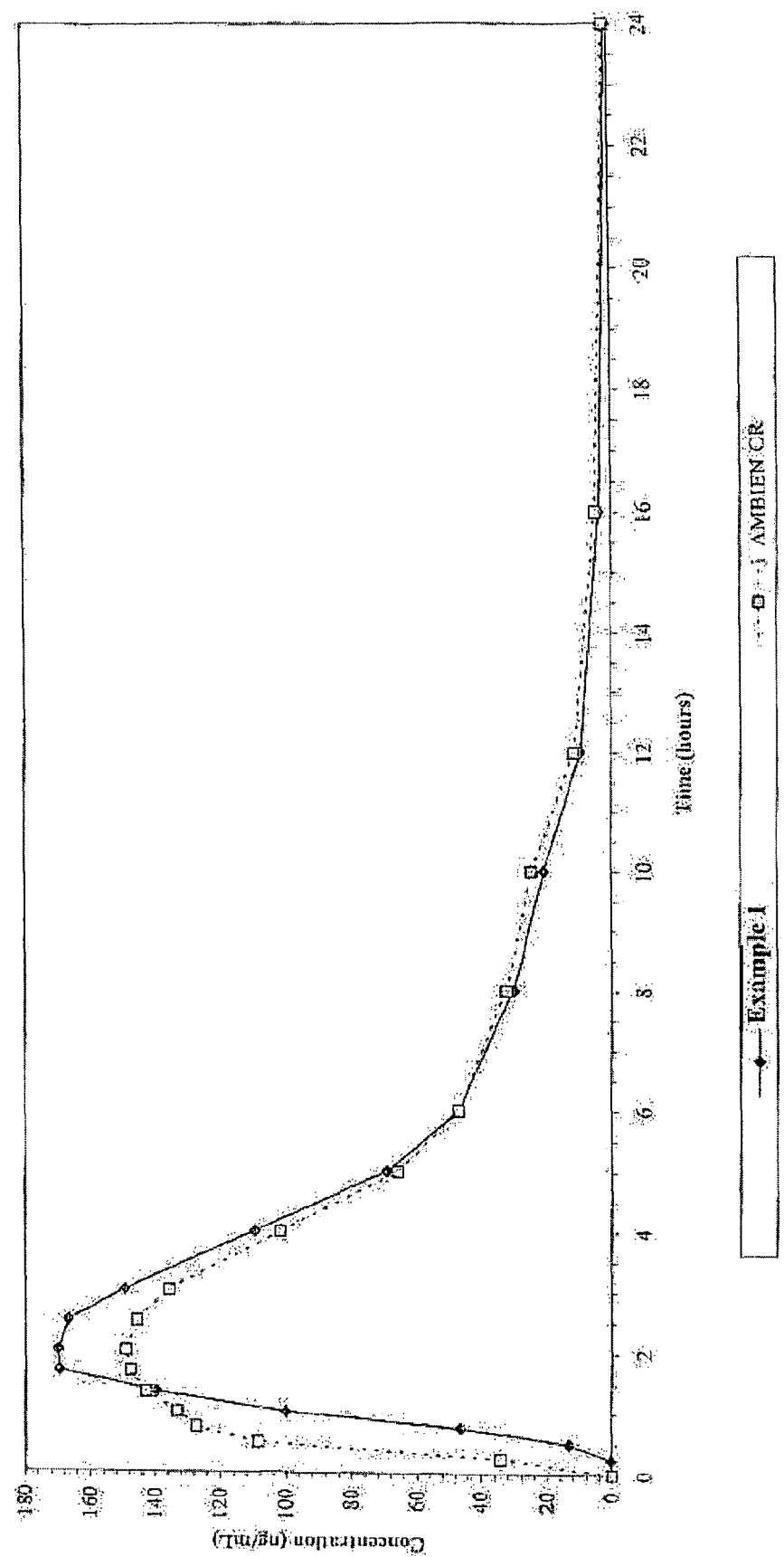
FIG. 2 is a graph of the mean plasma concentration for 47 subjects for the tablet prepared in Example 1 under fasting conditions.
Figure 3:
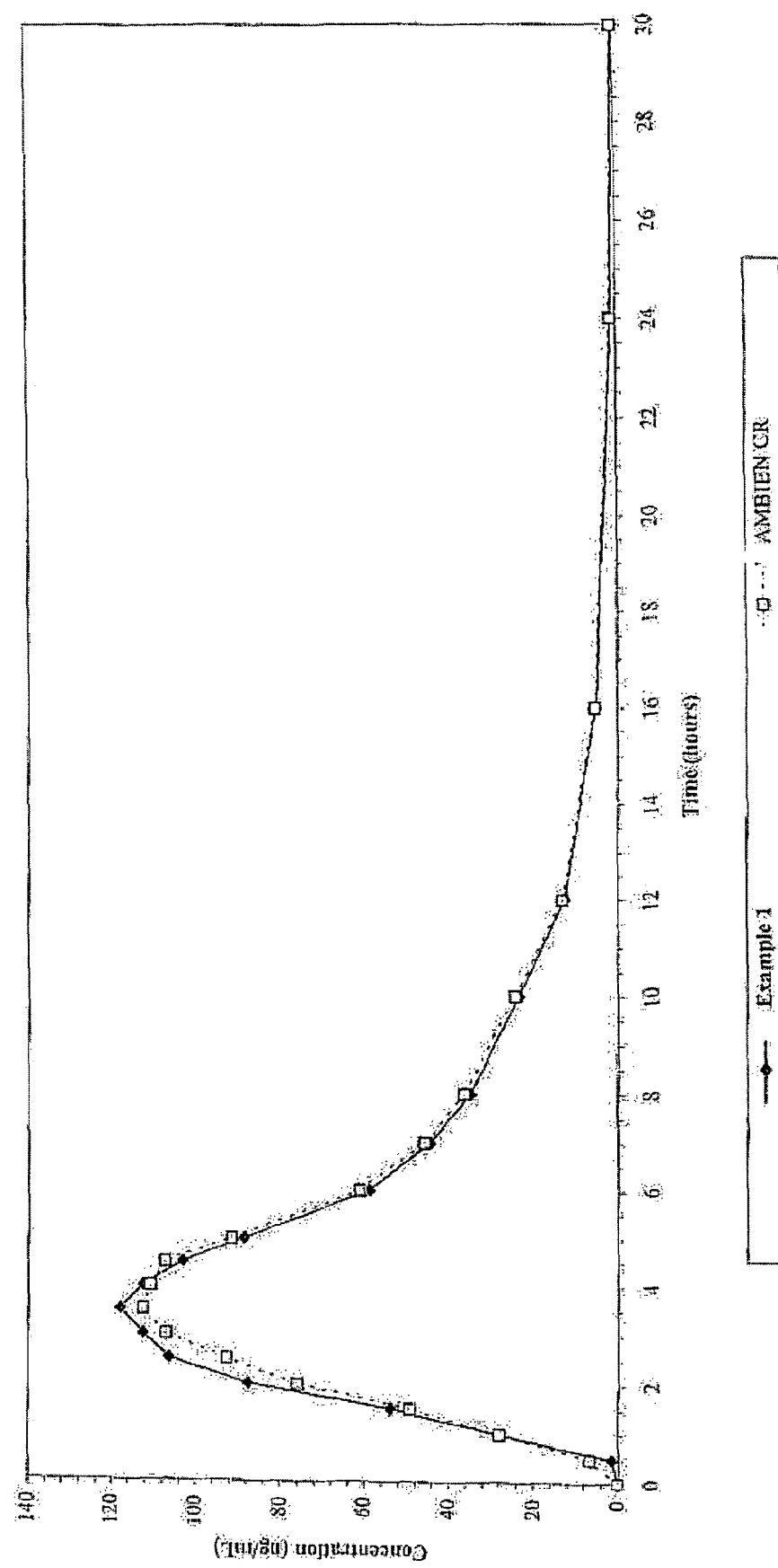
FIG. 3 is a graph of the mean plasma concentration for 48 subjects for the tablet prepared in Example 1 under non-fasting conditions.

Graphs of the mean plasma concentrations based upon the above biostudies are shown in FIGS. 2 and 3.

EXAMPLE 2

A 12.5 mg zolpidem tartrate tablet in accordance with the present invention was prepared as follows:

(a) Core 3.6 kg of microcrystalline cellulose (AVICEL PH 102), 1.44 kg of hydroxypropyl methylcellulose (METHOCEL K4M Premium CR Grade), 0.60 kg of zolpidem tartrate, 6.211 kg of anhydrous lactose (direct tableting grade) and 0.030 kg of colloidal silicon dioxide (CAB-O-SIL M-5P) were loaded into a one cubic foot V-Blender and blended for 20 minutes. The blended material was then passed through a comil fitted with an 1143 size stainless steel screen operating at a speed of about 1400 rpm. The screened material was blended in the one cubic foot blender for an additional 20 minutes. 0.12 kg of magnesium stearate was screened with a 30 mesh screen and added to the three cubic foot blender and blended for an additional 5 minutes. After all the ingredients were blended together, the mixture was compressed into tablets using a rotary press fitted with 0.3125" round standard concave punches. The target hardness was between 6-14 kp with a target weight of 250 mg.

(b) Non-Functional Coating 0.4689 kg of OPADRY II Coral 85G93099 was added to approximately 12.652 kg of purified water and mixed. The coating was applied to the core tablets prepared in step (a) using a 24" pan coating apparatus. The pan coater employed two spray guns located about 5-15 inches from the tablet bed, a pan speed of 3-12 rpms, a spray rate of 15-50 ml/min, an atomization pressure of 15-45 PSI, a pattern pressure of 15-45 PSI, air volume of 200-600 CFM and an exhaust temperature of 35-55 C. Approximately 0.00480 kg of Candelila wax was applied to the color coated tablets in the pan coater.

The final tablet had the following composition:

| Ingredient | mg/tablet |
|---|---|
| Core | |
| Zolpidem tartrate | 12.5 |
| Methocel K4M PCR | 30 |
| Avicel PH 102 | 75.0 |
| Anhydrous Lactose DC | 129.4 |
| Cab-O-Sil | 0.6.250 |
| Mg Stearate | 2.5 |
| Coating | |
| Candelilla Wax* | 0.10 |
| Opadry ® II Coral* | 7.5 |

*part of aesthetic coating (color and polishing)

Dissolutions studies for drug release from the formulation of Example 2 were conducted using a USP apparatus 2, 900 ml of 0.01N HCl at 50 rpms and 37° C. The results of the dissolution testing are:

| Time | % dissolved |
|---|---|
| 0.25 hour | 14 |
| 0.5 hours | 26 |
| 1 hours | 42 |
| 2 hours | 66 |
| 3 hours | 84 |
| 4 hours | 94 |
| 6 hours | 101 |

The tablet prepared in Example 2 was tested on 12 individuals in a single dose study according to FDA bioequivalence guidelines. The reference product for the study was a commercially available AMBIEN CR tablet. A summary of the biostudy results are reproduced below:

EXAMPLE 2

N=12 (Fasting)

Ln - Transformed Data

| PK Variable | Least Squares Mean Test | Least Squares Mean Reference | Geometric Mean Test | Geometric Mean Reference | % Ratio | 90% Confidence Level (Lower Limit, Upper Limit) |
|---|---|---|---|---|---|---|
| $C_{max}$ | 4.822 | 5.110 | 124.21 | 165.63 | 74.99 | (61.3, 91.74) |
| $AUC_{0-t}$ | 6.633 | 6.765 | 759.70 | 866.98 | 87.63 | (77.01, 99.7) |
| $AUC_{0-\infty}$ | 6.644 | 6.777 | 768.42 | 877.15 | 87.60 | (76.91, 99.79) |

-continued

Non-Transformed Data

| PK Variable | Least Squares Mean | | % Ratio | 90% Confidence Level (Lower Limit, Upper Limit) |
|---|---|---|---|---|
| | Test | Reference | | |
| $C_{max}$ | 138.68 | 172.51 | 80.39 | (62.69, 98.08) |
| $AUC_{0-t}$ | 840.68 | 915.04 | 91.87 | (83.86, 99.89) |
| $AUC_{0-\infty}$ | 849.77 | 924.62 | 91.90 | (83.86, 99.95) |
| $T_{max}$ | 3.92 | 1.30 | 302.77 | (239.7, 365.83) |
| $k_e$ | 0.2375 | 0.2331 | 101.89 | (89.48, 114.3) |
| $t_{1/2}$ | 3.22 | 3.21 | 100.60 | (90.57, 110.62) |

EXAMPLE 2

N=12 (Non-Fasting)

Ln - Transformed Data

| PK Variable | Least Squares Mean | | Geometric Mean | | % Ratio | 90% Confidence Level (Lower Limit, Upper Limit) |
|---|---|---|---|---|---|---|
| | Test | Reference | Test | Reference | | |
| $C_{max}$ | 4.853 | 4.776 | 128.14 | 118.58 | 108.06 | (85.75, 136.19) |
| $AUC_{0-t}$ | 6.262 | 6.400 | 524.38 | 602.13 | 87.09 | (71.37, 106.27) |
| $AUC_{0-\infty}$ | 6.277 | 6.429 | 532.31 | 619.57 | 85.91 | (69.55, 106.13) |

Non-Transformed Data

| PK Variable | Least Squares Mean | | % Ratio | 90% Confidence Level (Lower Limit, Upper Limit) |
|---|---|---|---|---|
| | Test | Reference | | |
| $C_{max}$ | 139.27 | 125.59 | 110.89 | (88.01, 133.78) |
| $AUC_{0-t}$ | 582.42 | 656.47 | 88.72 | (69.77, 107.67) |
| $AUC_{0-\infty}$ | 590.59 | 681.36 | 86.68 | (65.37, 107.98) |
| $T_{max}$ | 3.42 | 3.46 | 98.80 | (74.07, 123.52) |
| $k_e$ | 0.3264 | 0.3033 | 107.61 | (91.61, 123.62) |
| $t_{1/2}$ | 2.36 | 2.61 | 90.42 | (68.98, 111.85) |

Figure 4:
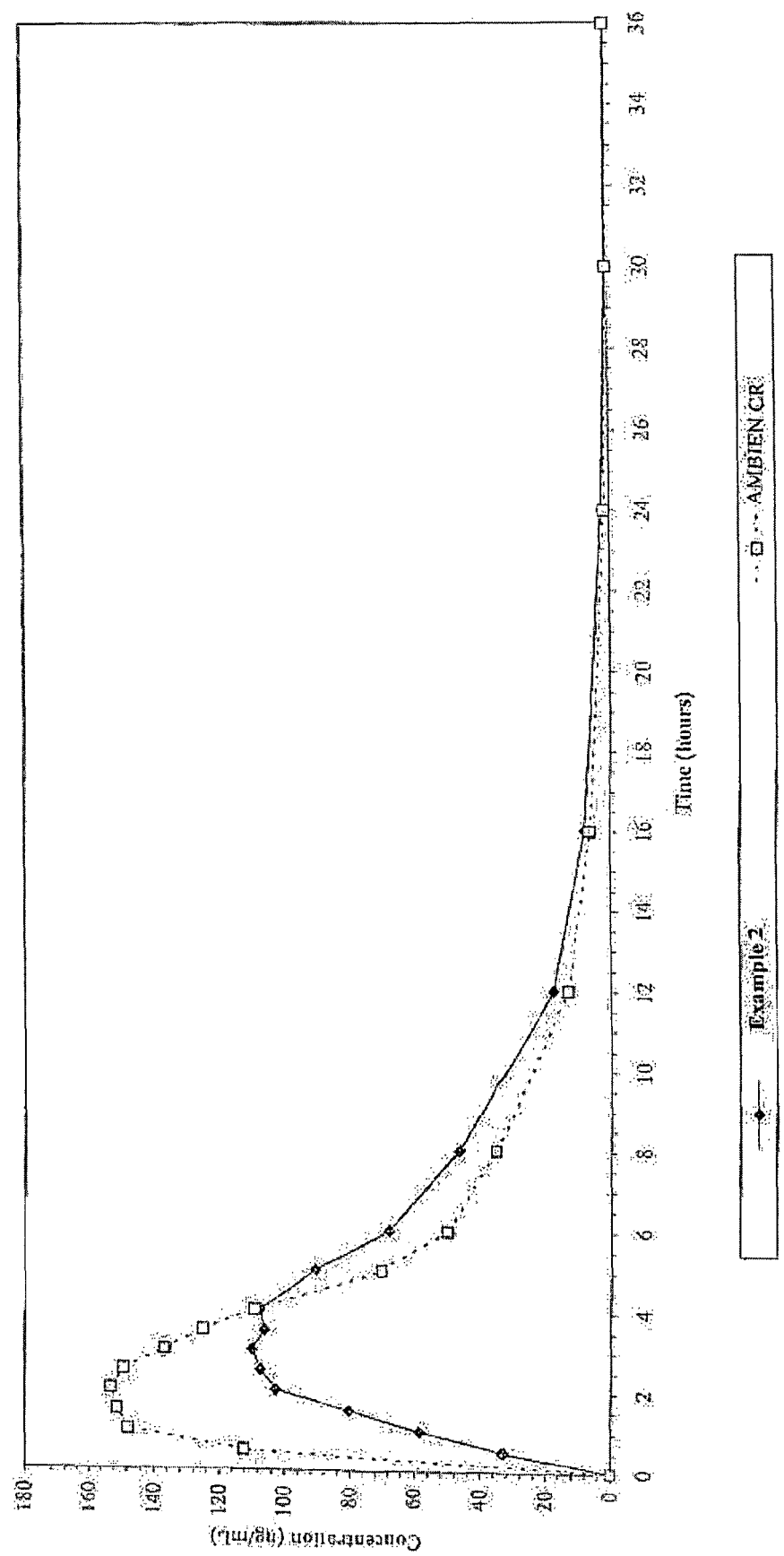
FIG. 4 is a graph of the mean plasma concentration for 12 subjects for the tablet prepared in Example 2 under fasting conditions.
Figure 5:
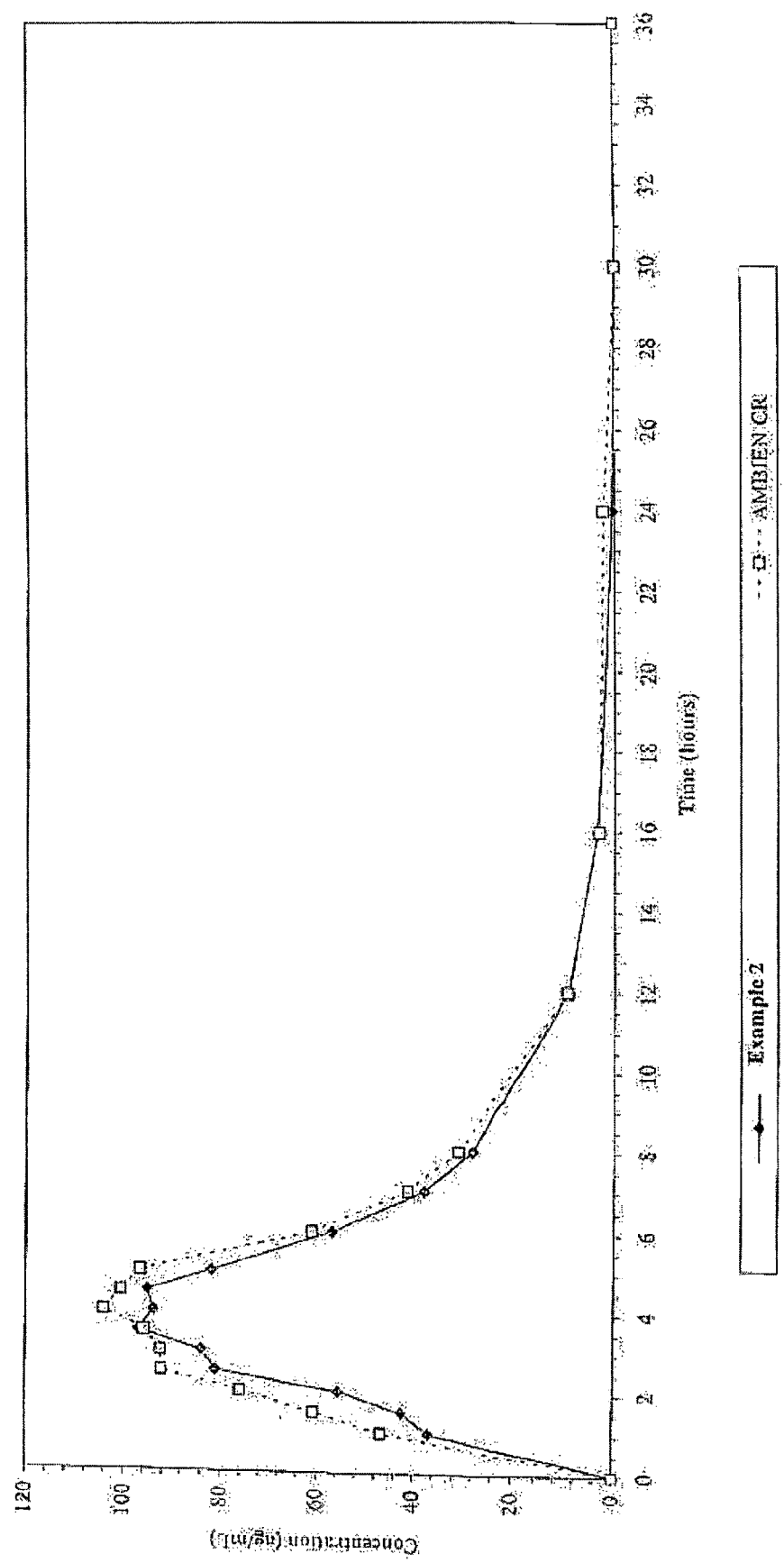
FIG. 5 is a graph of the mean plasma concentration for 12 subjects for the tablet prepared in Example 2 under non-fasting conditions.

Graphs of the mean plasma concentrations based upon the above biostudies are shown in FIGS. 4 and 5.

EXAMPLE 3

A 12.5 mg zolpidem tartrate tablet in accordance with the present invention was prepared as follows:
(a) Core 9.266 kg of microcrystalline cellulose (AVICEL PH 102), 1.875 kg of hydroxypropyl methylcellulose (METHOCEL K4M Premium CR Grade), 0.6250 kg of hydroxypropyl methylcellulose (METHOCEL K100M Premium CR), 1.563 kg of zolpidem tartrate, 17.53 kg of anhydrous lactose (direct tabletting grade) and 0.07813 kg of colloidal silicon dioxide (CAB-O-SIL M-5P) were loaded into a three cubic foot V-Blender and blended for 20 minutes. The blended material was then passed through a comil fitted with an 1143 size stainless steel screen operating at a speed of about 1400 rpm. The screened material was blended in the three cubic foot blender for an additional 20 minutes. 0.3125 kg of magnesium stearate was screened with a 30 mesh screen and added to the three cubic foot blender and blended for an additional 5 minutes. After all the ingredients were blended together, the mixture was compressed into tablets using a rotary press fitted with 0.3125" round standard concave punches. The target hardness was between 6-12 kp with a target weight of 250 mg.

The core tablets were coated with a pH dependent coating as follows:
(b) pH Dependent Coating 0.4335 kg of hydroxypropyl cellulose (KLUCEL EF) was added to approximately 20.37 kg of purified water and mixed until the hydroxypropyl cellulose was dissolved. Once the hydroxypropyl cellulose was dissolved approximately 0.8665 kg of an enteric methacrylic acid copolymer (ACRYL-EZE White) was added to the solution while mixing at high speed. The mixing continued for about 20 minutes until the enteric polymer was uniformly dispersed. The enteric polymer dispersion was applied to the core tablets prepared in step (a) using a 30" pan coating apparatus. The pan coater employed three spray guns located about 5-12 inches from the tablet bed, a pan speed of 3-14 rpms, a spray rate of 30-150 ml/min, an atomization pressure of 25-45 PSI, a pattern pressure of 25-45 PSI, air volume of 300-1200 CFM and an exhaust temperature of 35-55 C. The coating continued until the weight gain on 100 tablets was about 0.856 g per tablet. Once the target weight gain was obtained the tablets were rotated at 2-4 rpms for about 10 minutes to dry. Approximately 0.0125 kg of Candelila wax was then applied to the tablets in the pan coater.

The final tablet had the following composition:

| Ingredient | mg/tablet |
|---|---|
| Core | |
| Zolpidem tartrate | 12.5 |
| Methocel K4M PCR | 15.0 |
| Methocel K100M PCR | 5.0 |
| Avicel PH 102 | 74.13 |
| Anhydrous Lactose DC | 140.3 |
| Cab-O-Sil | 0.625 |
| Mg Stearate | 2.5 |
| Coating | |
| Acryl-Eze White | 5.333 |
| Klucel EF | 2.677 |
| Candelilla Wax* | 0.10 |

*part of aesthetic coating (polishing)

Dissolutions studies for drug release from the formulation of Example 3 were conducted using a USP apparatus 2, 900 ml of 0.01N HCl at 50 rpms and 37° C. The results of the dissolution testing are:

| Time | % dissolved |
|---|---|
| 0.25 hour | 15 |
| 0.5 hours | 29 |
| 1 hours | 49 |
| 2 hours | 73 |
| 3 hours | 90 |
| 4 hours | 98 |
| 6 hours | 101 |

The tablet prepared in Example 3 was tested on 11 individuals in a single dose study according to FDA bioequivalence guidelines. The reference product for the study was a commercially available AMBIEN CR tablet. A summary of the biostudy results are reproduced below:

EXAMPLE 3

N=11 (Fasting)

| | Ln - Transformed Data | | | | | | |
|---|---|---|---|---|---|---|---|
| | Least Squares Mean | | Geometric Mean | | | Mean Square | Interval (Lower Limit, Upper |
| PK Variable | A: Test | Reference | A: Test | Reference | % Ratio | Error | Limit) |
| $C_{max}$ | 5.271 | 5.137 | 194.62 | 170.25 | 114.32 | 0.02967 | (100.65, 129.85) |
| $AUC_{0-t}$ | 6.656 | 6.708 | 777.40 | 819.01 | 94.92 | 0.3196 | (83.17, 108.33) |
| $AUC_{0-\infty}$ | 6.667 | 6.720 | 785.89 | 829.09 | 94.79 | 0.03114 | (83.19, 108) |

| | Non-Transformed Data | | | | |
|---|---|---|---|---|---|
| | Least Squares Mean | | | | Interval (Lower Limit, |
| PK Variable | A: Test | Reference | % Ratio | Mean Square Error | Upper Limit) |
| $C_{max}$ | 206.28 | 183.62 | 112.34 | 1143.88 | (98.72, 125.96) |
| $AUC_{0-t}$ | 822.43 | 898.29 | 91.56 | 21199.75 | (79.57, 103.34) |
| $AUC_{0-\infty}$ | 831.16 | 908.39 | 91.50 | 21151.39 | (79.66, 103.34) |
| $T_{max}$ | 1.84 | 1.46 | 125.65 | 0.9654 | (75.92, 175.38) |
| $k_e$ | 0.2621 | 0.2317 | 113.13 | 0.00106 | (102.75, 123.50) |
| $t_{1/2}$ | 2.77 | 3.22 | 86.18 | 0.1475 | (77.36, 95.01) |

Figure 6:
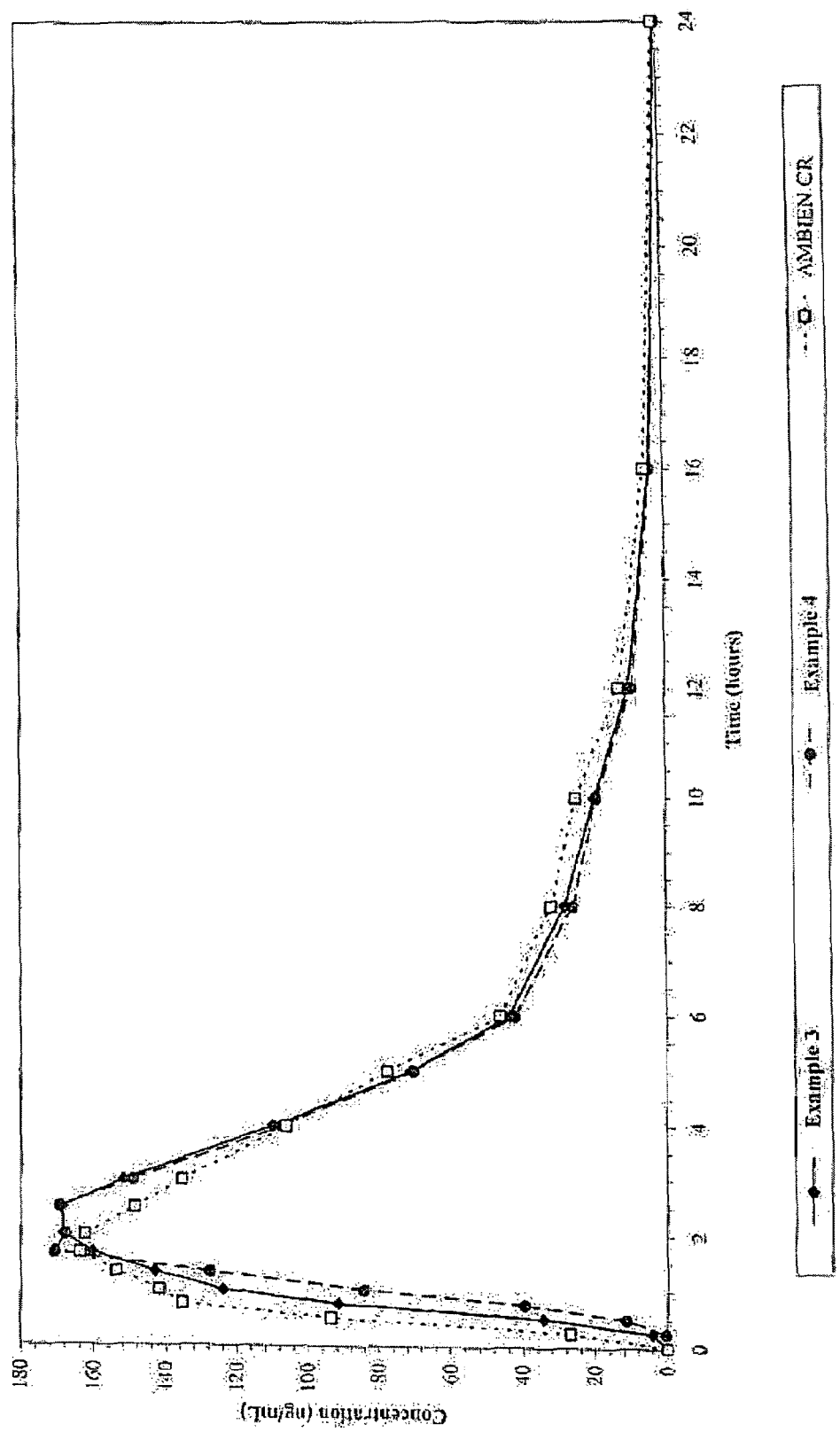
FIG. 6 is a graph of the mean plasma concentration for 12 subjects for the tablet prepared in Examples 3 and 4 under fasting conditions.

A graph of the mean plasma concentration based upon the above biostudy is shown in FIG. 6.

EXAMPLE 4

A 12.5 mg zolpidem tartrate tablet in accordance with the present invention was prepared as follows:
(a) Core 9.375 kg of microcrystalline cellulose (AVICEL PH 102), 1.563 kg of hydroxypropyl methylcellulose (METHOCEL K4M Premium CR Grade), 0.625 kg of hydroxypropyl methycellulose (METHOCEL K100M Premium CR Grade), 1.563 kg of zolpidem tartrate, 17.73 kg of anhydrous lactose (direct tableting grade) and 0.07813 kg of colloidal silicon dioxide (CAB-O-SIL M-5P) were loaded into a three cubic foot V-Blender and blended for 20 minutes. The blended material was then passed through a comil fitted with an 1143 size stainless steel screen operating at a speed of about 1400 rpm. The screened material was blended in the three cubic foot blender for an additional 20 minutes. 0.3125 kg of magnesium stearate was screened with a 30 mesh screen and added to the three cubic foot blender and blended for an additional 5 minutes. After all the ingredients were blended together, the mixture was compressed into tablets using a rotary press fitted with 0.3125" round standard concave punches. The target hardness was between 6-12 kp with a target weight of 250 mg.

The core tablets were coated with a pH dependent coating as follows:
(b) pH Dependent Coating 0.4773 kg of hydroxypropyl cellulose (KLUCEL EF) was added to approximately 29.91 kg of purified water and mixed until the hydroxypropyl cellulose was dissolved. Once the hydroxypropyl cellulose was dissolved approximately 1.432 kg of an enteric methacrylic acid copolymer (ACRYL-EZE White) was added to the solution while mixing at high speed. The mixing continued for about 20 minutes until the enteric polymer was uniformly dispersed. The enteric polymer dispersion was applied to the core tablets prepared in step (a) using a 30" pan coating apparatus. The pan coater employed three spray guns located about 5-12 inches from the tablet bed, a pan speed of 3-14 rpms, a spray rate of 30-150 ml/min, an atomization pressure of 25-45 PSI, a pattern pressure of 25-45 PSI, air volume of 300-1200 CFM and an exhaust temperature of 35-55 C. The coating continued until the weight gain on 100 tablets was about 1.223 g per tablet. Once the target weight gain was obtained the tablets were rotated at 2-4 rpms for about 10 minutes to dry. Approximately 0.01256 kg of Candelila wax was then applied to the tablets in the pan coater.

The final tablet had the following composition:

| Ingredient | mg/tablet |
|---|---|
| Core | |
| Zolpidem tartrate | 12.5 |
| Methocel K4M PCR | 12.5 |
| Methocel K100M PCR | 5.0 |
| Avicel PH 102 | 75.0 |
| Anhydrous Lactose DC | 141.9 |
| Cab-O-Sil | 0.625 |
| Mg Stearate | 2.5 |
| Coating | |
| Acryl-Eze White | 8.813 |
| Klucel EF | 2.937 |
| Candelilla Wax* | 0.10 |

*part of aesthetic coating (polishing)

Dissolutions studies for drug release from the formulation of Example 4 were conducted using a USP apparatus 2, 900 ml of 0.01N HCl at 50 rpms and 37° C. The results of the dissolution testing are:

| Time | % dissolved |
|---|---|
| 0.25 hour | 2 |
| 0.5 hours | 19 |
| 1 hours | 44 |
| 2 hours | 73 |
| 3 hours | 92 |
| 4 hours | 99 |
| 6 hours | 102 |

The tablet prepared in Example 4 was tested on 11 individuals in a single dose study according to FDA bioequivalence guidelines. The reference product for the study was a commercially available AMBIEN CR tablet. A summary of the biostudy results are reproduced below:

EXAMPLE 4

N=11 (Fasting)

| | Ln - Transformed Data | | | | | |
|---|---|---|---|---|---|---|
| | Least Squares Mean | | Geometric Mean | | | Mean Square Error | Interval (Lower Limit, Upper Limit) |
| PK Variable | B: Test | Reference | B: Test | Reference | % Ratio | | |
| $C_{max}$ | 5.252 | 5.137 | 191.01 | 170.25 | 112.20 | 0.02967 | (98.78, 127.44) |
| $AUC_{0-t}$ | 6.632 | 6.708 | 758.86 | 819.01 | 92.66 | 0.03196 | (81.18, 105.75) |
| $AUC_{0-\infty}$ | 6.643 | 6.720 | 767.60 | 829.09 | 92.58 | 0.03114 | (81.26, 105.49) |

| | Non-Transformed Data | | | | |
|---|---|---|---|---|---|
| | Least Squares Mean | | | | Interval (Lower Limit, Upper Limit) |
| PK Variable | B: Test | Reference | % Ratio | Mean Square Error | |
| $C_{max}$ | 199.60 | 183.62 | 108.70 | 1143.88 | (95.08, 122.32) |
| $AUC_{0-t}$ | 798.18 | 898.29 | 88.86 | 21199.75 | (76.87, 100.84) |
| $AUC_{0-\infty}$ | 807.13 | 908.39 | 88.85 | 21151.39 | (77.01, 100.69) |
| $T_{max}$ | 2.36 | 1.46 | 161.23 | 0.9654 | (111.50, 210.96) |
| $k_e$ | 0.2628 | 0.2317 | 113.42 | 0.00106 | (103.04, 123.79) |
| $t_{1/2}$ | 2.78 | 3.22 | 86.26 | 0.1475 | (77.43, 95.09) |

A graph of the mean plasma concentration based upon the above biostudy is shown in FIG. 6.

EXAMPLE 5

A 12.5 mg zolpidem tartrate tablet in accordance with the present invention was prepared using procedures similar to the procedures described in Example 1-4 except the tablets were made on a smaller laboratory scale. The tablet had the following composition:

| Core | % W/W (based on total weight of the core) |
|---|---|
| Zolpidem tartrate | 5.0 |
| Methocel K4M PCR | 8.0 |
| Avicel PH 102 | 30.0 |
| Anhydrous Lactose DC | 55.75 |
| Cab-O-Sil | 0.25 |
| Mg Stearate | 1 |

| Coating | % Weight based upon weight of the core |
|---|---|
| Eudragit RL 100 | 0.8534 |
| Eudragit E 100 | 1.280 |
| Triethyl citrate | 0.4286 |
| Talc | 1.420 |
| Lake blend green | 0.020 |

Dissolutions studies for drug release from the formulation of Example 5 were conducted using a USP apparatus 2, 900 ml of 0.01N HCl at 50 rpms and 37° C. The results of the dissolution testing are:

| Time | % dissolved |
|---|---|
| 0.25 hour | 8 |
| 0.5 hours | 28 |
| 1 hours | 50 |
| 2 hours | 82 |
| 3 hours | 97 |
| 4 hours | 102 |
| 6 hours | 103 |

While certain preferred and alternative embodiments of the invention have been set forth for purposes of disclosing the invention, modifications to the disclosed embodiments may occur to those who are skilled in the art. Accordingly, this specification is intended to cover all embodiments of the invention and modifications thereof which do not depart from the spirit and scope of the invention.

We claim:

1. A controlled release oral dosage form consisting of:
   (a) a unitary and homogeneous core comprising:
      (i) zolpidem tartrate; and
      (ii) about 3% to about 15% of a water soluble polymer that swells in the presence of water or gastro-intestinal fluids and exhibits a viscosity in a 2% aqueous solution of about 1,000 cps to about 120,000 cps; and
   (b) a pH dependent coating surrounding the homogeneous core comprising:
      (i) about 50% to about 80% by weight of the coating of an enteric polymer selected from the group consisting of zein, methacrylic acid copolymers, cellulose acetate phthalate, hydroxypropyl methylcellulose phthalate, hydroxypropyl methylcellulose acetate succinate, cellulose acetate trimellitate, polyvinyl acetate phthalate or mixtures thereof; and
      (ii) about 20% to about 50% by weight of the coating of a water soluble pore forming material selected from the group consisting of lactose, sucrose, fructose, mannitol, sorbitol, hydroxypropyl methylcellulose, hydroxypropyl cellulose, polyvinyl pyrrolidone, poloxamer, sodium lauryl sulfate, polysorbate, fumaric acid, succinic acid, citric acid, sodium chloride and potassium chloride; and
   (c) optionally an aesthetic coating surrounding the pH dependent coating;
   wherein all the zolpidem tartrate is present in the homogeneous core, the pH dependent coating comprises about 1 to about 20 weight percent of the dosage form and wherein the dosage form exhibits the following dissolution profile when tested in a USP apparatus 2, using 900 ml of 0.01 N HCl at 50 rpms and 37° C.:
      not more than 35% of the zolpidem is released within 0.5 hours;
      30-75% of the zolpidem is released within 1 hour;
      not less than 45% of the zolpidem is released within 2 hours; and
      not less than 85% of the zolpidem is released within 8 hours.

2. The controlled release dosage form as defined in claim 1 wherein the core further comprises a diluent.

3. The controlled release dosage form as defined in claim 2 wherein the diluent further comprises a mixture of water soluble material and water insoluble material.

4. The controlled release dosage form as defined in claim 1 wherein the pH dependent coating comprises about 2 to about 15 weight percent of the dosage form.

5. The controlled release dosage form as defined in claim 4 wherein the pH dependent coating comprises about 3 to about 10 weight percent of the dosage form.

6. The controlled release dosage form as defined in claim 1 wherein the water soluble polymer that swells in the presence of water or gastro-intestinal fluids has a molecular weight between 5,000 and 1,000,000.

7. The controlled release dosage form as defined in claim 1 that exhibits the following dissolution profile when tested in a USP apparatus 2, using 900 ml of 0.01 N HCl at 50 rpms and 37° C.:
   not more than 30% of the zolpidem is released within 0.5 hours;
   not less than 50% of the zolpidem is released within 2 hours; and
   not less than 90% of the zolpidem is released within 8 hours.

8. A controlled release oral tablet consisting of:
   (a) a unitary and homogeneous core consisting of:
      (i) zolpidem tartrate; and
      (ii) about 3% to about 15% based upon the weight of the homogeneous core of a water soluble polymer that swells in the presence of water or gastro-intestinal fluids and exhibits a viscosity in a 2% aqueous solution of about 2,000 cps to about 120,000 cps selected from the group consisting of polyvinyl pyrrolidone, methylcellulose, hydroxymethyl cellulose, polyethylene oxide polymers, hydroxyethyl cellulose, hydroxypropyl cellulose, hydroxypropyl methylcellulose and mixtures thereof;
      (iii) a diluent; and
      (iv) optionally one or more of a lubricant, glidant, stabilizer, antifoaming agent, colorant, and dispersing aid;
   (b) a pH dependent coating surrounding the homogeneous core consisting of:
      (i) about 50% to about 80% by weight of the coating of a methacrylic acid copolymer; and
      (ii) about 20% to about 50% by weight of the coating of a water soluble pore forming material selected from the group consisting of lactose, sucrose, fructose, mannitol, sorbitol, hydroxypropyl methylcellulose, hydroxypropyl cellulose, polyvinyl pyrrolidone, poloxamer, sodium lauryl sulfate, polysorbate, fumaric acid, succinic acid, citric acid, sodium chloride and potassium chloride;
      (iii) optionally one or more of a plasticizer, antifoaming agent, dispersing aid, surfactant, anti-sticking agent, colorant, pigment and polishing aid; and
   (c) optionally an aesthetic coating surrounding the pH dependent coating;
   wherein all the zolpidem tartrate is present in the homogeneous core, the pH dependent coating comprises about 2 to about 15 weight percent of the dosage form and wherein the dosage form exhibits the following dissolution profile when tested in a USP apparatus 2, using 900 ml of 0.01 N HCl at 50 rpms and 37° C.:
      not more than 35% of the zolpidem is released within 0.5 hours;
      30-75% of the zolpidem is released within 1 hour;
      not less than 45% of the zolpidem is released within 2 hours; and
      not less than 85% of the zolpidem is released within 8 hours.

9. The controlled release tablet of claim 8 wherein the water soluble polymer that swells in the presence of water or gastro-intestinal fluids is a hydroxypropyl methylcellulose.

10. The controlled release tablet of claim 8 wherein the water soluble polymer that swells in the presence of water or gastro-intestinal fluids has a molecular weight between 5,000 and 1,000,000.

* * * * *